United States Patent [19]

Good

[11] Patent Number: 5,487,660
[45] Date of Patent: Jan. 30, 1996

[54] ORTHODONTIC APPARATUS

[76] Inventor: Jackson J. Good, 501 N. 13th St., Norfolk, Nebr. 68701

[21] Appl. No.: 290,490

[22] Filed: Aug. 12, 1994

[51] Int. Cl.⁶ .............................. A61C 3/00; A61C 5/00
[52] U.S. Cl. .................... 433/3; 433/93; 433/140
[58] Field of Search .............................. 433/2, 3, 4, 93, 433/94, 141, 140; 128/12, 861

[56] References Cited

U.S. PATENT DOCUMENTS

| | | | |
|---|---|---|---|
| 2,396,619 | 3/1946 | Strayer | 433/4 |
| 3,686,762 | 8/1972 | Sutter | 433/3 |
| 3,924,333 | 12/1975 | Erickson | 32/33 |
| 4,167,814 | 9/1979 | Schubert | 32/33 |
| 4,971,557 | 11/1990 | Martin | 433/140 |
| 4,975,057 | 12/1990 | Dyfvermark | 433/93 |
| 4,992,046 | 2/1991 | Sharp | 433/93 |
| 5,039,302 | 8/1991 | Keys | 433/141 |
| 5,152,686 | 10/1992 | Duggan et al. | 433/93 |
| 5,235,991 | 8/1993 | Minneman | 433/140 |

*Primary Examiner*—Cary E. O'Connor
*Attorney, Agent, or Firm*—Zarley, McKee, Thomte, Voorhees & Sease; Mark D. Frederiksen

[57] ABSTRACT

An orthodontic apparatus includes a mouth prop for separating a patient' lips to provide access to the teeth, and a placement tool for placing orthodontic brackets on a patient's teeth. The mouth prop includes a flat platform which is inserted between the patient's upper and lower teeth to provide a base upon which a head portion of the placement tool may be supported to align a bracket on a tooth. The mouth prop preferably includes a fluid ejector tube affixed to the rearward edge of the platform to remove fluids from the patient's mouth during the procedure. The placement tool includes a head portion having a support plate for releasably securing a bracket during the positioning process. A leg affixed to the head portion support plate depends a predetermined distance and supports the bracket above the mouth prop platform at a desired height. The process of attaching the brackets includes the steps of securing a bracket to the placement tool head portion and applying an adhesive to the seat of the bracket. The placement tool head is then positioned on the mouth prop platform with the lower end of the head portion depending leg in contact with the platform to space the bracket a predetermined distance from the platform. The bracket is then placed into contact with the tooth to secure the bracket in position. The bracket is then disconnected from the placement tool and additional brackets are located in a similar fashion, all having uniform spacing from the platform so as to align the brackets uniformly on the teeth.

15 Claims, 3 Drawing Sheets

ORTHODONTIC APPARATUS

TECHNICAL FIELD

The present invention relates generally to an orthodontic apparatus for propping portions of the mouth open during the placement of orthodontic brackets, and more particularly to an orthodontic apparatus which permits accurate placement and alignment of brackets on a patient's teeth.

BACKGROUND OF THE INVENTION

The placement of brackets on teeth in orthodontic procedures are difficult to accurately align on the teeth in order to provide the most effective use of the appliances. While various appliances have been utilized in the prior art to isolate or open parts of the mouth to facilitate the performance of various dental services, such prior art devices suffer several problems.

Bite blocks and expansion forceps have been used to hold a patient's jaws open. Rubber dams and clamps are also commonly used, by placing flexible pieces of material having holes therethrough over the patient's teeth so that the teeth protrude through the holes. However, none of these prior devices assist the orthodontist in accurately placing and aligning brackets on the teeth. In fact, in many cases, the location of such brackets are merely placed by eye, without measurement.

SUMMARY OF THE INVENTION

It is therefore a general object of the present invention to provide an improved orthodontic apparatus for accurately placing and aligning brackets on the teeth.

A further object is to provide an orthodontic apparatus which opens the patient's mouth to provide access to a plurality of the patient's teeth.

Still another object of the present invention is to provide an orthodontic apparatus which incorporates a saliva ejector to prevent contamination.

These and other objects will be apparent to those skilled in the art.

The orthodontic apparatus of the present invention includes a mouth prop for separating a patient's lips to provide access to the teeth, and a placement tool for placing orthodontic brackets on a patient's teeth. The mouth prop includes a flat platform which is inserted between the patient's upper and lower teeth to provide a base upon which a head portion of the placement tool may be supported to align a bracket on a tooth. The mouth prop preferably includes a fluid ejector tube affixed to the rearward edge of the platform to remove fluids from the patient's mouth during the procedure. The placement tool includes a head portion having a support plate for releasably securing a bracket during the positioning process. A leg affixed to the head portion support plate depends a predetermined distance and supports the bracket above the mouth prop platform at a desired height. The process of attaching the brackets includes the steps of securing a bracket to the placement tool head portion and applying an adhesive to the seat of the bracket. The placement tool head is then positioned on the mouth prop platform with the lower end of the head portion depending leg in contact with the platform to space the bracket a predetermined distance from the platform. The bracket is then placed into contact with the tooth to secure the bracket in position. The bracket is then disconnected from the placement tool and additional brackets are located in a similar fashion, all having uniform spacing from the platform so as to align the brackets uniformly on the teeth.

DESCRIPTION OF THE PREFERRED EMBODIMENT

Figure 1:
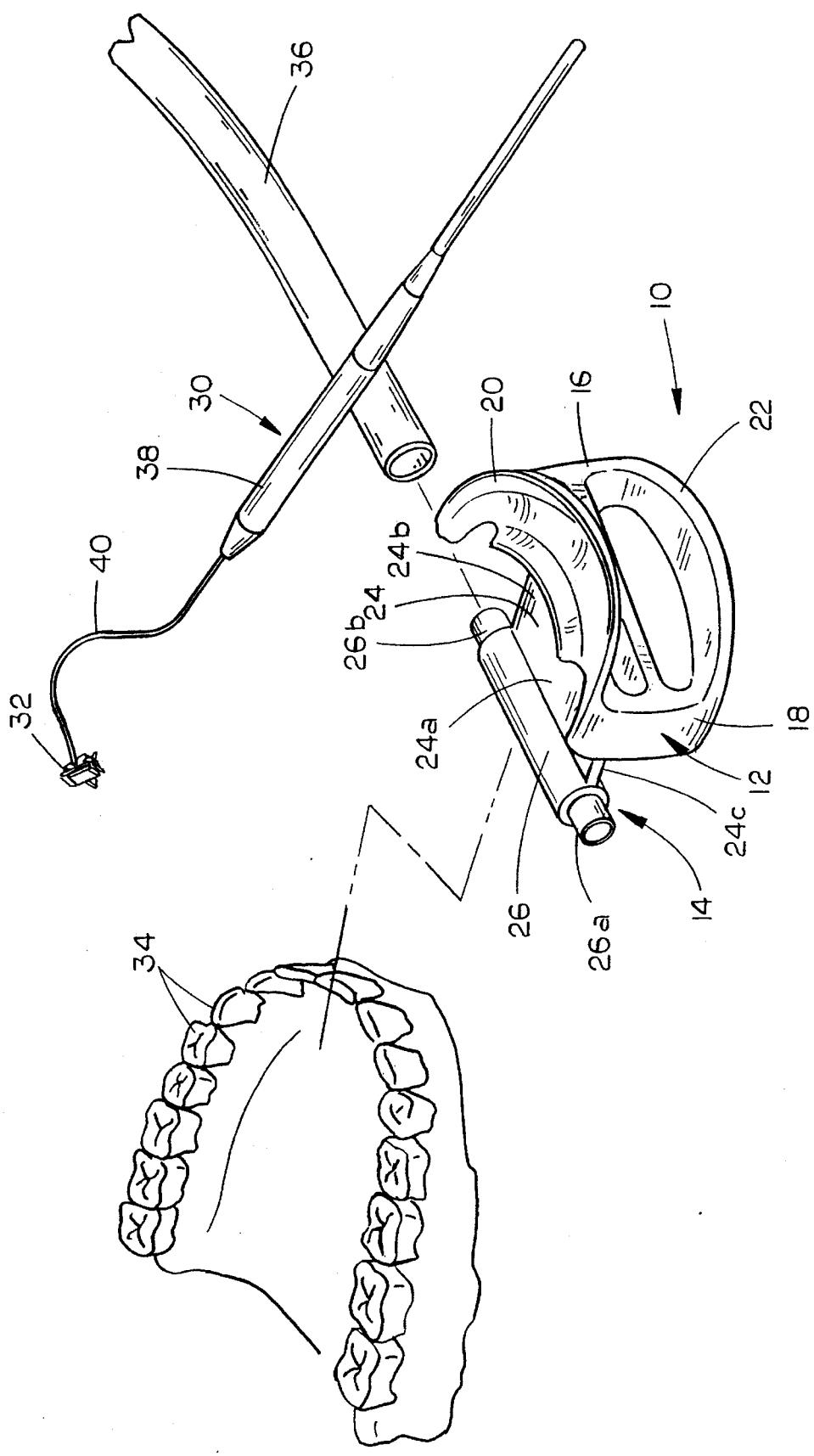
FIG. 1 is a perspective view of the orthodontic apparatus and a placement tool for use with the apparatus, associated with a lower jaw.

Referring now to the drawings, in which similar or corresponding parts are identified with the same reference numeral, and more particularly to FIG. 1, the orthodontic apparatus of the present invention is designated generally at 10 and includes a mouth prop 12 and a fluid ejector 14.

Figure 3:
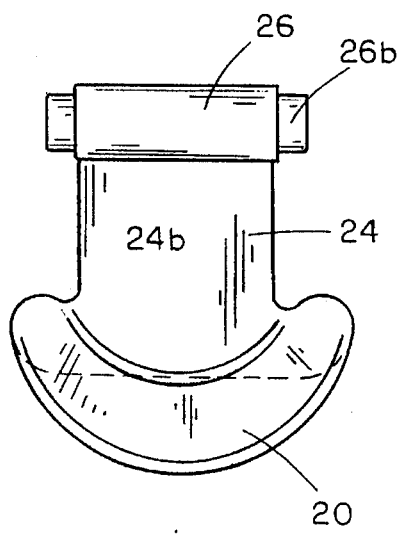
FIG. 3 is a top plan view of the apparatus shown in FIGS. 1 and 2.
Figure 4:
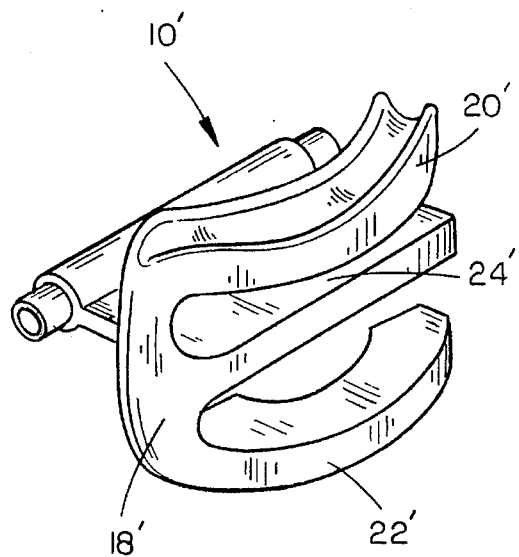
FIG. 4 is an enlarged perspective view of a second embodiment of the orthodontic apparatus.

Mouth prop 12 includes right and left generally vertical walls 16 and 18 respectively, with an upper lip holder 20 and a lower lip holder 22 affixed between the upper and lower ends thereof respectively. Upper lip holder 20 is a generally arc-shaped channel which is curved to follow the curvature of the upper lip of a patient. Lower lip holder 22 is similarly curved to comfortably support the patient's lower lip. As shown in FIGS. 3 and 4, the curvature of the arc of lip holders 20 and 22 may be adjusted for the particular portion of the mouth to be supported by the orthodontic apparatus 10. Apparatus 10' in FIG. 4 has a lesser curvature on lip holders 20 and 22, which is more readily utilized along the sides of the mouth, while orthodontic apparatus 10 of FIG. 3 is preferably utilized for the front of the mouth, where the curvature is greater.

Referring once again to FIG. 1, a flat support platform 24 is affixed horizontally between right and left walls 16 and 18, and spaced generally centrally between upper and lower lip holders 20 and 22. Support platform 24 extends rearwardly to a rearward end 24a upon which fluid ejector 14 is mounted. Platform 24 has a flat upper surface 24b and lower surface 24c which provide a base upon which placement tool 30 is supported during positioning of brackets 32 on the teeth 34.

Fluid ejector 14 includes a hollow tube 26 having a pair of tubular shoulders 26a and 26b on the opposing ends, to receive an end of a flexible hose 36, used to carry fluids and contaminants from fluid ejector 14 away from the patient's mouth. The opposite end of tube 26 will accept a conventional suction tube.

Figure 2:
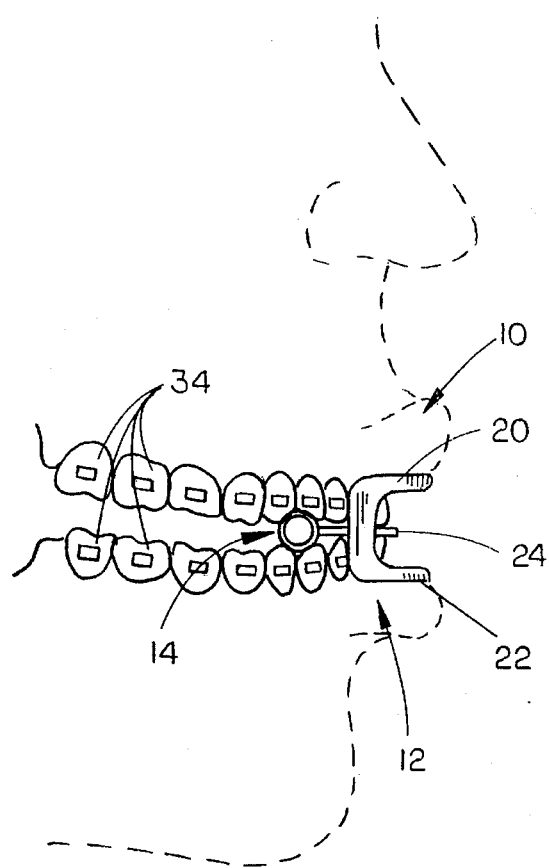
FIG. 2 is a side elevational view of the apparatus inserted in a patient's mouth.

As shown in FIG. 2, orthodontic apparatus 10 is positioned in a patient's mouth with the patient griping platform 24 with the teeth 34. Patient's upper lip is supported in upper lip holder 20, and the patient's lower lip is supported in lower lip holder 22, so as to separate the lips and provide an access space to the teeth 34 between upper and lower lip holders 20 and 22.

Referring now to FIG. 3, orthodontic apparatus 10' includes the same upper and lower lip holders 20' and 22', but with a curvature less than that of apparatus 10, to more appropriately fit the side of the mouth. However, only one vertical wall 18' is utilized to affix lip holders 20' and 22' and platform 24', so that the opposing end remains open (towards the front of the mouth) to permit easier access.

Figure 5:
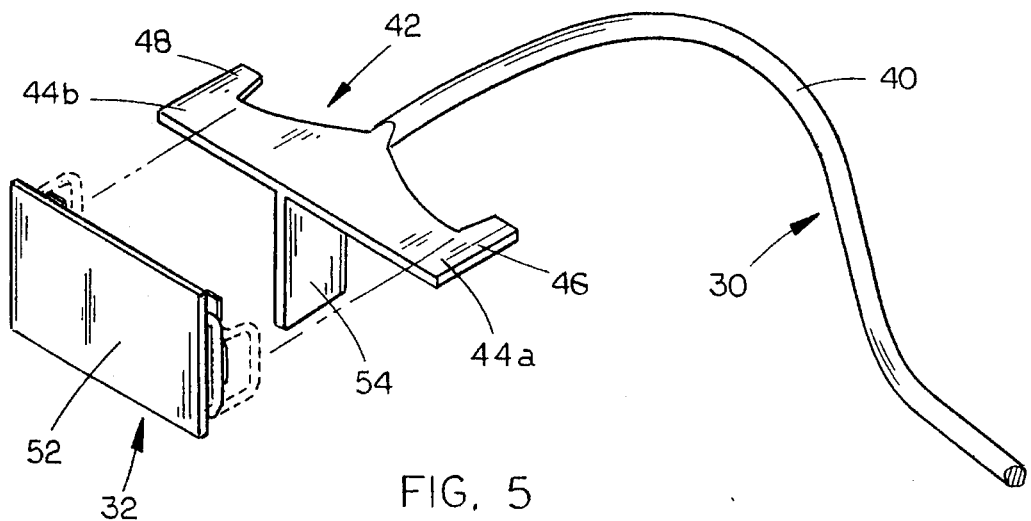
FIG. 5 is an enlarged perspective view of the placement tool of the present invention with an orthodontic bracket removed from the head thereof.

Referring once again to FIG. 1, placement tool 30 includes an elongated handle 38 with a bent wire 40 projecting from the forward end of handle 38 in a conventional hook shape. FIG. 5 shows the placement tool head 42 mounted on the forward end of bent wire 40, which is utilized to support a conventional orthodontic bracket 32 during placement of the bracket on a tooth.

Figure 6:
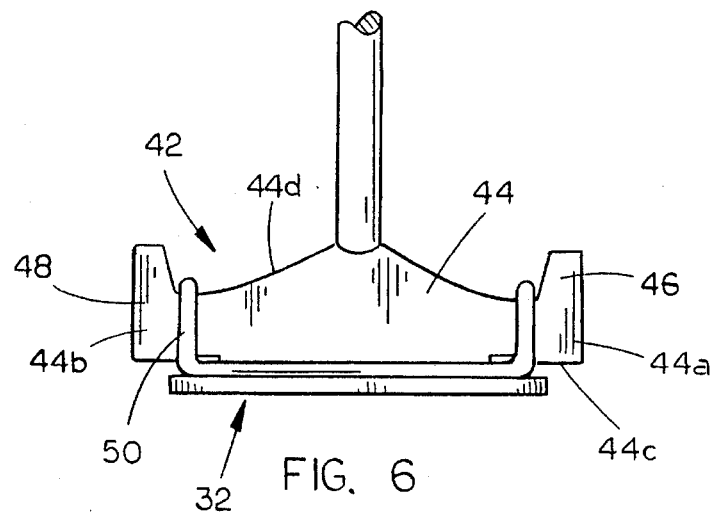
FIG. 6 is a top plan view of the placement tool with a bracket connected thereto.

Placement tool head 42 includes a generally horizontally oriented plate 44 with rearwardly projecting wings 46 and 48 at the opposing ends 44a and 44b. Wings 46 and 48 extend rearwardly from the forward edge 44c of plate 44, farther than the remaining rearward edge 44d of plate 44, such that the rubber band 50 of bracket 32 may be stretched around each wing 46 and 48 to retain bracket 32 in position on head 42, as shown in FIG. 6. The generally vertically oriented and flat seat 52 of bracket 32 is thereby positioned generally perpendicularly to plate 44 when rubber band 50 is stretched around wings 46 and 48.

A leg 54 depends from the plate 44 generally centrally between wings 46 and 48, as shown in FIG. 5. Leg 54 has a predetermined length, for a purpose described in more detail hereinbelow.

Figure 7:
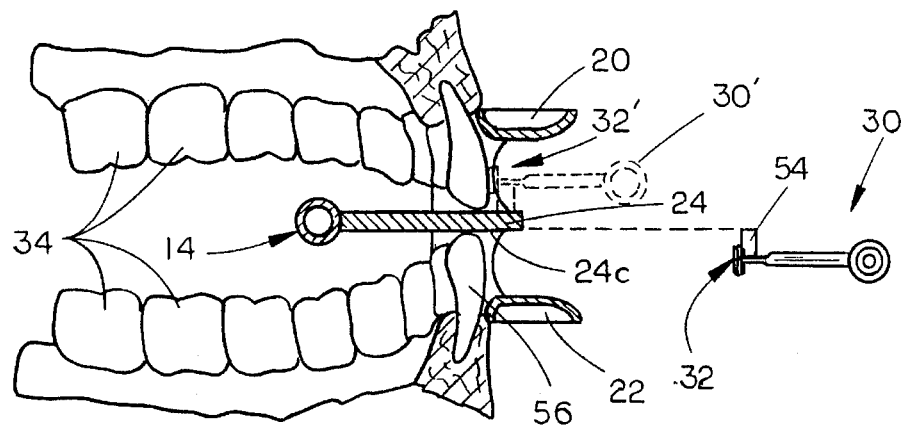
FIG. 7 is a vertical sectional view through the orthodontic apparatus located in a patient's mouth, with the placement tool aligned therewith.

The procedure for utilizing orthodontic apparatus 10 and placement tool 30 begins with the step of placement of orthodontic apparatus 10 in the patient's mouth, as shown generally in FIG. 2. Apparatus 10 is located in that portion of the mouth where brackets 32 are to be placed on teeth 34. As shown in FIG. 7, fluid ejector 14 is located within the mouth adjacent the teeth to be bracketed, and thereby ejects fluids to prevent contamination of the area. In FIG. 7, tooth 56 is the first tooth to be fitted with a bracket 32.

A bracket 32 is connected to the head 42 of a placement tool 30, as shown in FIG. 5. The placement tool is then moved to the patient's mouth with the leg 54 positioned on the lower surface 24c of platform 24. The orthodontist may select the appropriate length leg 54 on the head 42 for a particular patient, in order to generally center bracket 32 on teeth 34. Adhesive is applied to the seat portion of bracket 32 and leg 54 is moved rearwardly towards tooth 56 while in constant contact with platform 24. Because a number of teeth 34 are exposed between upper and lower lip holders 20 and 22, brackets 32 will be uniformly positioned on teeth 34, spaced equal distances from platform 24.

Whereas the invention has been shown and described in connection with the preferred embodiment thereof, it should be understood that many modifications, substitutions and additions may be made which are within the intended broad scope of the appended claims.

I claim:

1. An orthodontic apparatus comprising:

an upper lip support connected to and spaced vertically above a lower lip support;

a generally horizontal, flat platform affixed generally midway between the upper and lower lip supports; and a pair of generally vertical, spaced apart walls interconnecting the upper and lower lip supports and forming an access opening between said walls and lip supports for access to a patient's teeth above and below said platform.

2. The orthodontic apparatus of claim 1, wherein said upper and lower lip supports are generally parallel and curve rearwardly in an arc from a forward edge to a pair of rearward ends.

3. The orthodontic apparatus of claim 2, wherein said platform extends rearwardly from said walls beyond the rearward extent of said support rearward ends.

4. The orthodontic apparatus of claim 3, further comprising a hollow tube mounted to the rearward end of the platform, having first and second ends, and a flexible hose connected to the tube first end for draining fluid from said tube.

5. The orthodontic apparatus of claim 4, wherein said tube includes a plurality of perforations for the passage of fluid into the tube.

6. The orthodontic apparatus of claim 4, further comprising means on said tube first and second ends for removably connecting said flexible hose, to permit connection of said hose to either of said first and second ends.

7. A placement tool for placing an orthodontic bracket on a tooth, comprising:

a handle having forward and rearward ends;

a head connected to the handle forward end for releasably securing a bracket to be placed on a tooth;

said head including a generally horizontal plate with forward and rearward edges, opposing side edges, and upper and lower surfaces;

said plate including a pair of spaced apart wing portions extending rearwardly beyond an intermediate rearward edge of the plate; and a leg depending from the plate lower surface and having a predetermined length as measured from the plate lower surface to a leg lower end.

8. The placement tool of claim 7, wherein said leg is mounted perpendicularly to said plate.

9. Apparatus for aligning orthodontic brackets on teeth, comprising:

a mouth prop having an upper lip support connected to and spaced vertically above a lower lip support;

said mouth prop including a generally horizontal, flat platform affixed generally midway between the upper and lower lip supports;

a pair of generally vertical, spaced apart walls interconnecting the upper and lower lip supports and forming an access opening between said walls and lip supports for access to a patient's teeth above and below said platform; and a placement tool for placing a bracket, including a handle with a head connected to a forward end;

said head including a generally horizontal plate with forward and rearward edges, opposing side edges, and upper and lower surfaces;

said placement tool head further comprising a leg depending from the plate lower surface and having a predetermined length as measured from the plate lower surface to a lower end of the leg.

10. The orthodontic apparatus of claim 9, wherein said upper and lower lip supports are generally parallel and curve rearwardly in an arc from a forward edge to a pair of rearward ends.

11. The orthodontic apparatus of claim 10, wherein said platform extends rearwardly from said walls beyond the rearward extent of said support rearward ends.

12. The orthodontic apparatus of claim 11, further comprising a hollow tube mounted to the rearward end of the platform, having first and second ends, and a flexible hose connected to the tube first end for draining fluid from said tube.

13. The orthodontic apparatus of claim 12, wherein said tube includes a plurality of perforations for the passage of fluid into the tube.

14. An orthodontic apparatus, comprising:

an upper lip support connected to and spaced vertically above a lower lip support;

a generally horizontal, flat platform affixed generally midway between the upper and lower lip supports; and a generally vertical wall interconnecting the upper and lower lip supports and forming an access opening between the lip supports and adjacent the wall for access to a patient's teeth above and below said platform.

15. A method for placing an orthodontic bracket on a tooth, comprising the steps of:

inserting an orthodontic apparatus having a flat platform and lip supports into a patient's mouth with a forward platform edge projecting outwardly from the patient's teeth and the lip supports located to separate and support the patient's lips to form an access opening along the forward edge of the platform for accessing the patient's teeth;

selecting a placement tool having a head portion with a bracket support plate and a depending leg, the depending leg having a predetermined length;

connecting an orthodontic bracket to the support plate of the placement tool head;

applying an adhesive to a seat portion of the bracket, for securing the bracket to a tooth;

contacting a lower end of the head portion leg on the platform upper surface with the bracket adjacent a predetermined tooth;

sliding the head portion towards the tooth until the bracket seat portion is adhered to the tooth with said adhesive; and disconnecting the first bracket from the placement tool after the adhesive has set.

\* \* \* \* \*